United States Patent [19]

Joseph et al.

[11] Patent Number: 4,655,349
[45] Date of Patent: Apr. 7, 1987

[54] SYSTEM FOR AUTOMATICALLY INSPECTING TRANSPARENT CONTAINERS FOR SIDEWALL AND DIMENSIONAL DEFECTS

[75] Inventors: James R. Joseph, DuBois; James F. Wesdock, Reynoldsville; Allen Lerch; Ronald Chollock, both of DuBois; John Waugaman, Brockway; Glenn Lindberg, Brockport; James R. Wymer, Brookville; Brad Brennen, St. Marys, all of Pa.

[73] Assignee: Brockway, Inc., Brockway, Pa.

[21] Appl. No.: 686,525

[22] Filed: Dec. 27, 1984

[51] Int. Cl.⁴ .................................. B07C 5/342
[52] U.S. Cl. ........................... 209/524; 209/526; 209/588; 250/223 B; 250/563; 356/240
[58] Field of Search ........... 209/522, 523, 524, 526, 209/588, 576, 577, 579; 356/240, 428; 250/223 B, 563

[56] References Cited

U.S. PATENT DOCUMENTS

| | | | |
|---|---|---|---|
| 3,356,853 | 12/1967 | Rottmann | 209/526 |
| 3,411,009 | 11/1968 | Ford et al. | 250/223 B |
| 3,770,969 | 11/1973 | Ansevin et al. | 209/526 |
| 4,076,424 | 2/1978 | Ida | 356/418 |
| 4,280,624 | 7/1981 | Ford | 209/524 |
| 4,338,028 | 7/1982 | Trailleur et al. | 356/240 |
| 4,378,494 | 3/1983 | Miller | 209/526 |
| 4,454,542 | 6/1984 | Miyazawa | 209/526 |
| 4,513,868 | 4/1985 | Culling et al. | 209/587 |

FOREIGN PATENT DOCUMENTS 2080946 2/1982 United Kingdom ............... 356/240

Primary Examiner—Robert B. Reeves
Assistant Examiner—Donald T. Hajec
Attorney, Agent, or Firm—Burns, Doane, Swecker & Mathis

[57] ABSTRACT

A system for automatically detecting sidewall and dimensional defects in a transparent container includes a laser scanning system positioned astride a conveyor in a production line. In an upstream inspection zone a laser beam vertically scans a portion of the side wall of the container. Photosensors positioned in a detection chamber detect the specific effect which any defect has upon the laser beam by determining the location of light passing through the container and comparing its intensity against pre-set thresholds. A flaw signal is generated when a threshold is exceeded. The number of flaw signals is counted and when the count equals a pre-set value a reject signal is generated to eject the defective container from the conveyor. If a container is not rejected, it passes through a rotator assembly which rotates the container precisely 90°. The container then continues to a similar downstream inspection zone where an identical scanning and detection process is repeated with regard to the previously uninspected portions of the side wall of the container.

26 Claims, 5 Drawing Figures

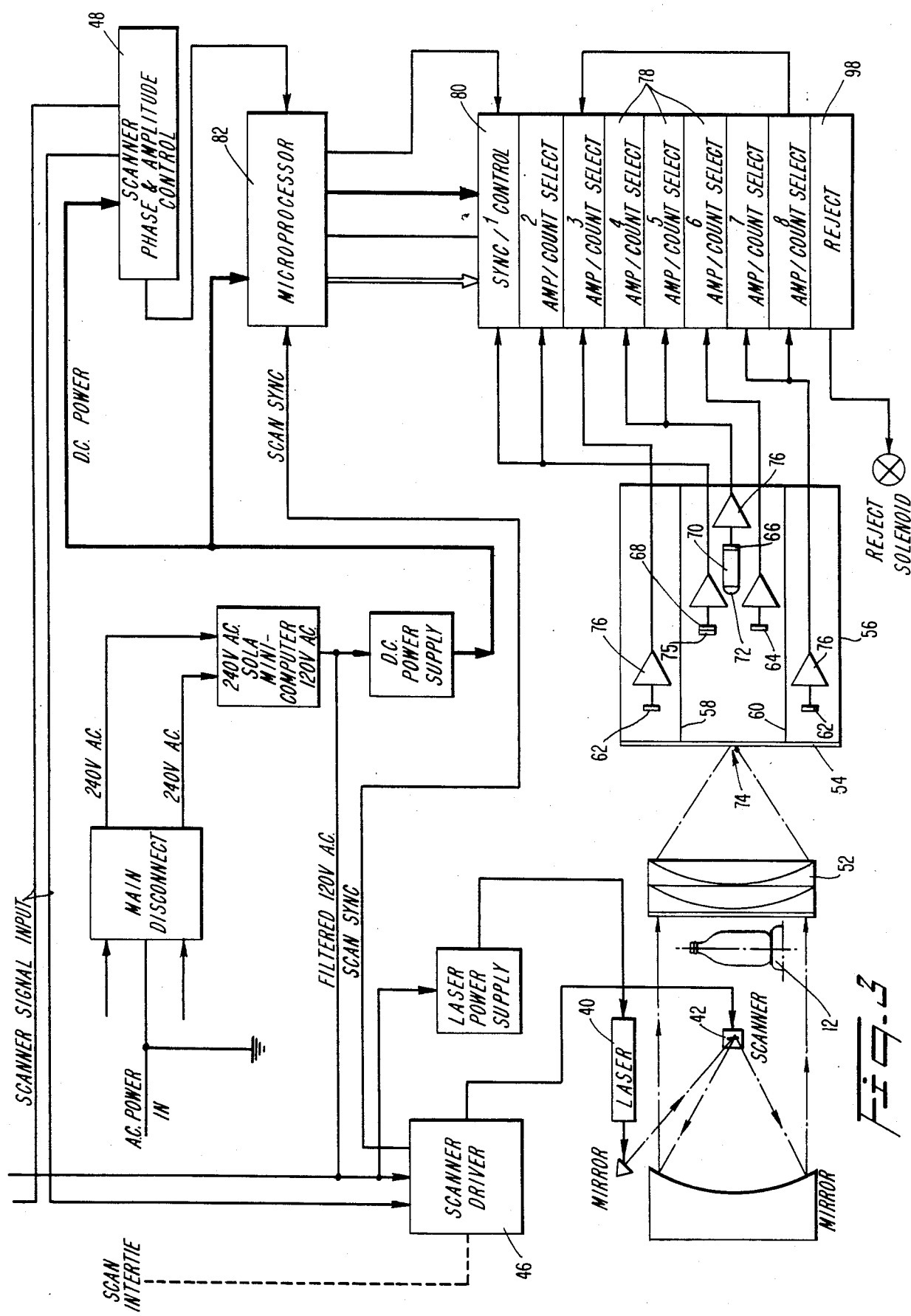

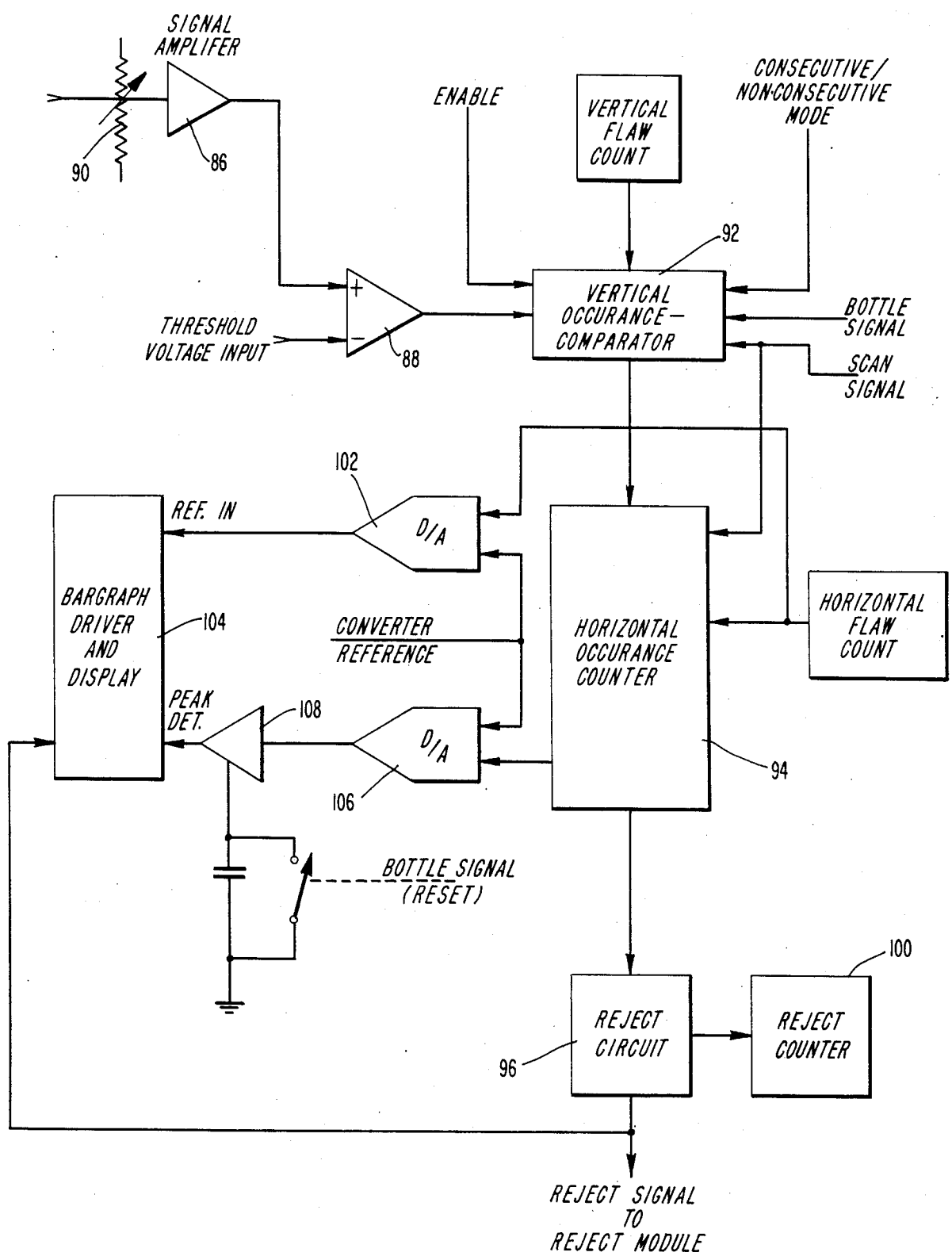

SYSTEM FOR AUTOMATICALLY INSPECTING TRANSPARENT CONTAINERS FOR SIDEWALL AND DIMENSIONAL DEFECTS

BACKGROUND OF THE INVENTION

The present invention relates to a system for automatically detecting defects in articles that are produced from transparent materials. In particular, the invention is directed to the automatic inspection of transparent containers such as glass and plastic bottles.

Glass bottles and other transparent containers are subject to a number of different types of defects that can be occasioned by impurities within the glass material itself, by improper molding techniques resulting in fissures and non-uniform glass distribution, or by rough handling procedures. Accordingly, the bottles must be individually inspected to reject faulty ones after they emerge from an annealing lehr and before they are filled or shipped. In the past, such inspection has been carried out visually by human inspectors. However, such an approach is not entirely satisfactory not only because of the labor expenses that are incurred but also because of the inconsistencies that can result from human error. For example, as the inspector grows tired near the end of an inspection period he is more likely to miss a fault in a bottle that quickly passes through an inspection station.

More recently, various types of systems have been proposed for automatically inspecting defects in bottles. Example of such systems are disclosed in U.S. Pat. Nos. 4,165,277 and 4,338,028. These prior systems are generally limited to the detection of one flaw, or at most a few types of flaws, such as side fissures, for example. Accordingly, the requirement for a human inspector still exists because of the likelihood that flaws other than those detected by the automatic systems could be present. Moreover, these systems may be less effective than a human inspector in terms of the percentage of faulty containers that are detected.

Furthermore, when the same type of defect consistently occurs during production it is desirable to locate the source of the flaw and correct it. While a human inspector may be able to do this, heretofore known automatic systems do not provide such a capability. Thus, the prior systems are not totally satisfactory from the standpoint of eliminating the need for visual inspection.

OBJECTS AND BRIEF STATEMENT OF THE INVENTION

Accordingly, it is a general object of the present invention to provide a novel system for automatically detecting defects in articles that are produced from transparent materials.

It is a more specific object of the invention to provide such a system that is capable of detecting any and all of the various types of sidewall and dimensional defects that are commonly encountered in a transparent container with greater effectiveness than an average human inspector.

It is a further object of the present invention to provide such a system that also offers the capability of isolating the location and type of defects found in containers to better enable the source of the defect to be corrected, and thereby increase productivity.

Briefly, according to the present invention, these and other objects are achieved by means of a laser scanning system positioned astride a conveyer in a production line. In an upsteam inspection zone a laser beam vertically scans a portion of the side wall of the container. When no defect is present within the side wall, the laser beam passes essentially unimpeded through the container. However, if the beam strikes a defect in the container, beam propagation is effected by attenuation, dispersion, refraction, reflection, blocking or some combination of these effects in dependence upon the particular type of defect. Photosensors positioned in a detection chamber detect the specific effect which the defect has upon the laser beam by determining the location of light passing through the container and comparing its intensity against pre-set thresholds. A flaw signal is generated when a threshold is exceeded. The number of flaw signals is counted and when the count equals a pre-set value a reject signal is generated to eject the defective container from the conveyor.

If a container successfully passes through the upstream inspection zone without rejection, it continues to a rotator assembly which rotates the container precisely 90°. The container then passes through a similar downstream inspection zone where an identical scanning and detection process is repeated with regard to the previously uninspected portions of the side wall of the container.

Further features and advantages of the invention are explained in greater detail hereinafter with reference to a preferred form of the invention illustrated in the accompanying drawings.

BRIEF DESCRIPTION OF THE DRAWINGS

FIG. 3 is a partial block and partial schematic electrical and optical circuit diagram illustrating the components of one of the inspection zones;

FIG. 5 is a block circuit diagram of an amplifier and count selection circuit.

DESCRIPTION OF THE ILLUSTRATED EMBODIMENT

In the following description of a preferred embodiment of the invention, particular reference is made to the inspection of glass bottles in order to facilitate an understanding of the invention. However, it will be appreciated that the invention is not limited to this specific application. Rather, it can find a variety of applications in the inspection of almost any type of article made from a transparent material.

Figure 1:
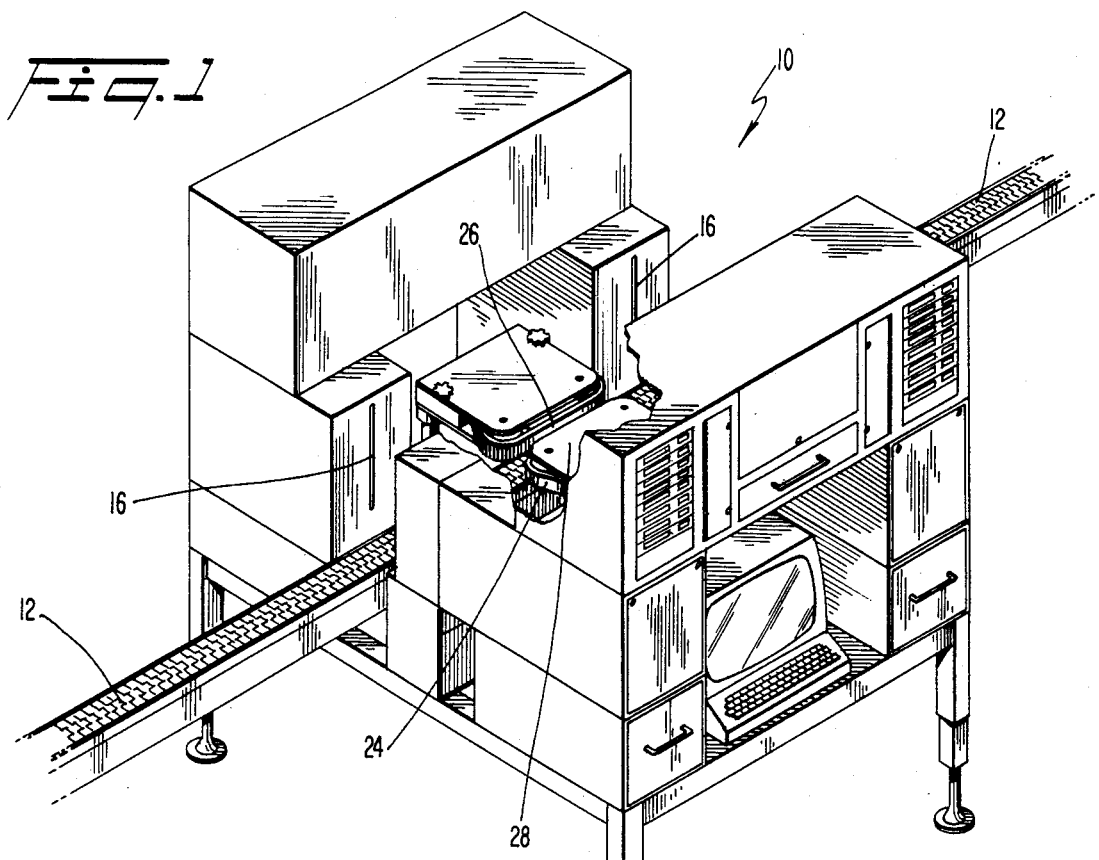
FIG. 1 is a perspective view of an electronic container inspecting station incorporating the present invention.
Figure 2:
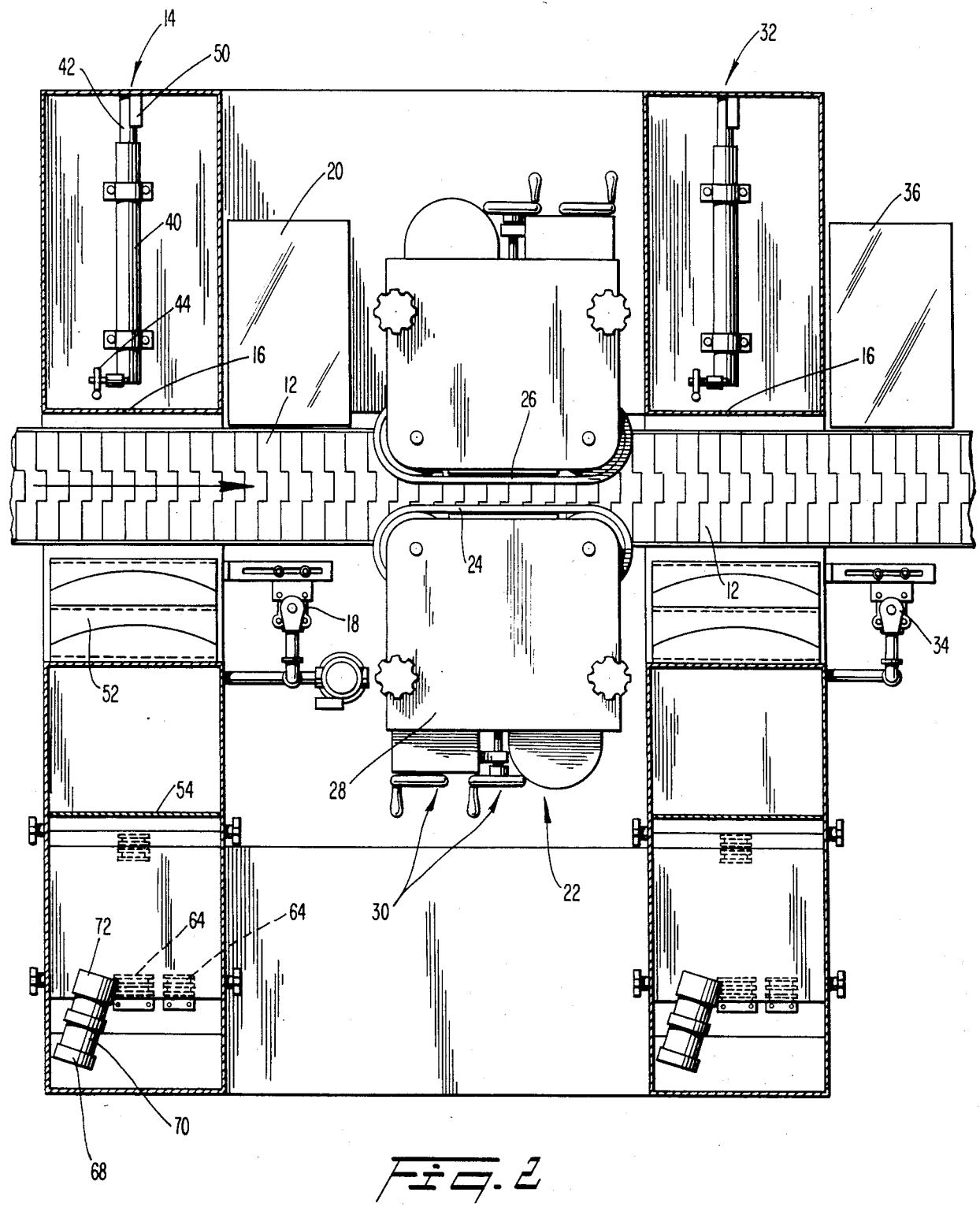
FIG. 2 is a cross-sectional top view of the inspection station.

Referring to FIGS. 1 and 2, bottles to be inspected are presented to an inspection station 10 in an upright position by means of a continuously moving conveyor 12, such as a table-top chain. The inspection station 10 might be located downstream of an annealing/cooling lehr in a bottle manufacturing facility. Suitable means (not shown) can be provided upstream of the inspection station to space the bottles and thereby control container throughput into the inspection station. In addition, a downed bottle remover can be located immediately upstream of the inspection station to prevent fallen or stuck bottles from being conveyed into the inspection station.

Within the inspection station 10, the bottles first pass through an upstream inspection zone 14. At this location, the bottles are traversed by a vertically scanned laser beam that passes through a slot 16 in a side wall of the inspection station cabinet adjacent the conveyor. The laser light passing through the bottle is collected on the opposite side of the conveyor and processed to determine whether any defects are present in the bottle. If a defect is detected, a reject signal is generated to cause the defective bottle to be removed from the conveyor. For example, the reject signal might actuate a solenoid that opens an air valve 18 located downstream of the inspection zone 14. When the valve is opened, pressurized air blows the rejected bottle off the conveyor into a cullet chute 20, which carries the rejected bottle to a disposal location.

Although the laser beam scans the entire bottle as it passes through the inspection zone 14, it will be appreciated that the beginning and end of the scan of each bottle will not provide significant defect information since the beam will be highly attenuated as it passes through the leading and trailing surfaces of the bottle. Accordingly, it is desirable to limit defect detection to that portion of the bottle scan in which the beam passes through the front and back walls of the bottle, as viewed in the direction of propagation of the beam. For example, as explained in greater detail hereinafter, the front 90° of circumference of the bottle and the back 90° of circumference might be inspected at the upstream zone 14.

If no defect is detected in the inspected portion of the bottle, it continues downstream on the conveyor 12 to a bottle rotator mechanism 22. The rotator mechanism includes a pair of spaced belts 24, 26 that are disposed parallel to the direction of travel of the bottles. The belts are spaced so that they can frictionally engage the opposite sides of the bottle. For this purpose they are covered with foam rubber or other suitable material to provide good contact with the bottles. In order to accommodate different sizes of bottles, the belts are housed within movable carriages 28. Jacks 30 are located on the carriages to enable them to be moved toward and away from one another to accommodate bottles of different widths, as well as up and down to accommodate bottles of different heights.

The two belts are driven at different speeds, one being slightly faster than the speed of the conveyor 12 and the other slightly slower, so as to rotate the bottle exactly 90° about its longitudinal axis as it travels at conveyor belt speed through the bottle rotator mechanism. Specifically, the speeds of the belts 24, 26 are defined as follows:

$$V_{B1} = V_C \left(1 + \frac{\pi D}{K}\right)$$

$$V_{B2} = V_C \left(1 - \frac{\pi D}{K}\right)$$

where $V_{B1}$ is the velocity of the faster belt, $V_{B2}$ is the velocity of the slower belt, $V_C$ is the velocity of the conveyor 12, D is the diameter of the bottle and K is a constant related to the length of travel of the bottle as it is being rotated in the rotator mechanism.

The speeds of the motors which respectively drive the belts 24 and 26 are coordinated by means of a motor speed ratio controller (not shown). One of the motors, e.g., the motor for the faster belt, functions as the lead or master motor, and the ratio controller controls the speed of the slower motor so as to maintain the relationship defined by the foregoing equations. Depending on the spacing of bottles on the conveyor, it may be possible to have more than one bottle in the rotator mechanism at a time.

After having been rotated by 90°, the bottles are presented to a downstream inspection zone 32 that is similar to the upstream zone 14. In this zone the bottles are scanned by a laser beam which is processed to detect faults in the portions of the bottle that were not inspected in the upstream location. If a fault is detected in this zone, a second air valve 34 can be actuated by means of a reject signal to blow the faulty bottle into a second cullet chute 36. If no defect is detected, the conveyor 12 carries the bottle away from the inspection station for further processing or filling.

Referring now to FIG. 3, the optical and electrical components for scanning the bottle and processing the light at one of the zones 14 or 32 to detect a flaw are shown in greater detail. A similar arrangement is present in the other zone. The laser beam is generated by a suitable linear polarized laser 40, such as a helium-neon laser. The output beam from this laser is reflected by a mirror 42 to a self-resonant optical scanner 44. The scanner 44 basically comprises a planar mirror that is pivoted about an axis of rotation parallel to the direction of movement of the bottles. The pivoting of the mirror about the axis of rotation is carried out by means of a scanner driver 46 under the control of a scanner phase and amplitude control circuit 48. Preferably, the scanner phase control circuit coordinates the phase of the scanning laser beam to the electronic synchronization signals while the scanner amplitude control circuit maintains a constant scan amplitude.

The sinusoidal scanning beam that is reflected from the scanner mirror is directed onto a spherical mirror 50 which reflects the scanning beam as parallel rays in a vertical plane. This plane is disposed transverse to the direction of movement of the bottle. The reflected beam passes through the slot 16 in the cabinet and traverses a vertical line along the bottle of the conveyor 12.

The laser light which passes through the bottle is projected onto a diffusing screen 54 that can be made of flashed opal glass or plastic. In order to increase the sensitivity of the system, the laser light passing through the bottle is first collected on the side of the conveyor opposite the laser by a dual plano-convex lens set 52 and focussed upon the screen. The screen 54 forms the front of an essentially light-tight detection chamber 56. This chamber is divided into three cells by means of partitions 58 and 60. If desired, the partitions can be vertically adjustable to accommodate bottles of different heights and/or shapes. A photodiode or other suitable type of light sensor 62 is located in each of the upper and lower cells to detect laser light which impinges on the portions of the screen corresponding to the location of these cells. The middle cell has three photodiodes 64, 66 and 68. One of these photodiodes 66 is mounted in a tube 70 having a focusing lens 72 that is oriented on the focal point 74 of the lens set 52 at the center of the screen 54. Another photodiode 68 in the central cell is provided with a laser line filter 75 which eliminates ambient lighting.

In operation, the scanner 44 can be operated at a frequency of about 800 Hz, for example, to scan a number of adjacent vertical traces on each bottle as it is being conveyed through an inspection zone. When the laser beam passes through the bottle essentially unimpeded, due to the absence of any defects, the lens system 52 focusses the laser light upon the focal point 74 at the center of the screen. However, if the beam strikes an imperfection within the bottle, it will either be blocked by the defect or it will be attenuated, dispersed, refracted, or reflected, or undergo some combination of these effects, in dependence upon the type of defect. The particular effect which the defect has on the beam will be detected by one or more of the photodiodes.

Each of the photodiodes 62–68 is connected to a preamplifier 76 and the amplified signal therefrom is presented to one or more amplifier and count selection circuits 78. In addition, the output signal from the filtered photosensor 68 within the central cell is presented to a synchronization and control circuit 80. The circuits 78 and 80 which are connected to the photosensors 64, 66 and 68 in the center cell are responsive to the absence of light, i.e. light intensity falling below a pre-selected threshold. In contrast, the circuits 78 that are connected to the photosensors 62 in the outer cells are responsive to the presence of light. Thus, if the light beam passing through a bottle is dispersed or refracted, some or all of the light will be projected onto the outer portion of the screen 54 where it will be detected by one or both of the photodiodes 62 in the upper and lower cells. If the beam is blocked or highly attenuated, the absence of light in the center cell will be detected by one or more of the photosensors 64, 66 and 68. For example, waviness in the wall of the bottle could displace the focussed light from the central spot 74, which will be sensed by the focussed photosensor 66.

The synchronization and control circuit 80 and the amplifer and count selection circuits 78 operate under the control of a microprocessor 82 to compare the intensity of the light detected by each of the photosensors 62–68 to preselected threshold levels and to generate a reject signal when a threshold is crossed a predetermined number of times. In particular, the microprocessor selectively actuates each of the amplifier and count selection circuits in accordance with a specific, adjustable inspection window which encompasses a portion of the container surface.

Figure 4:
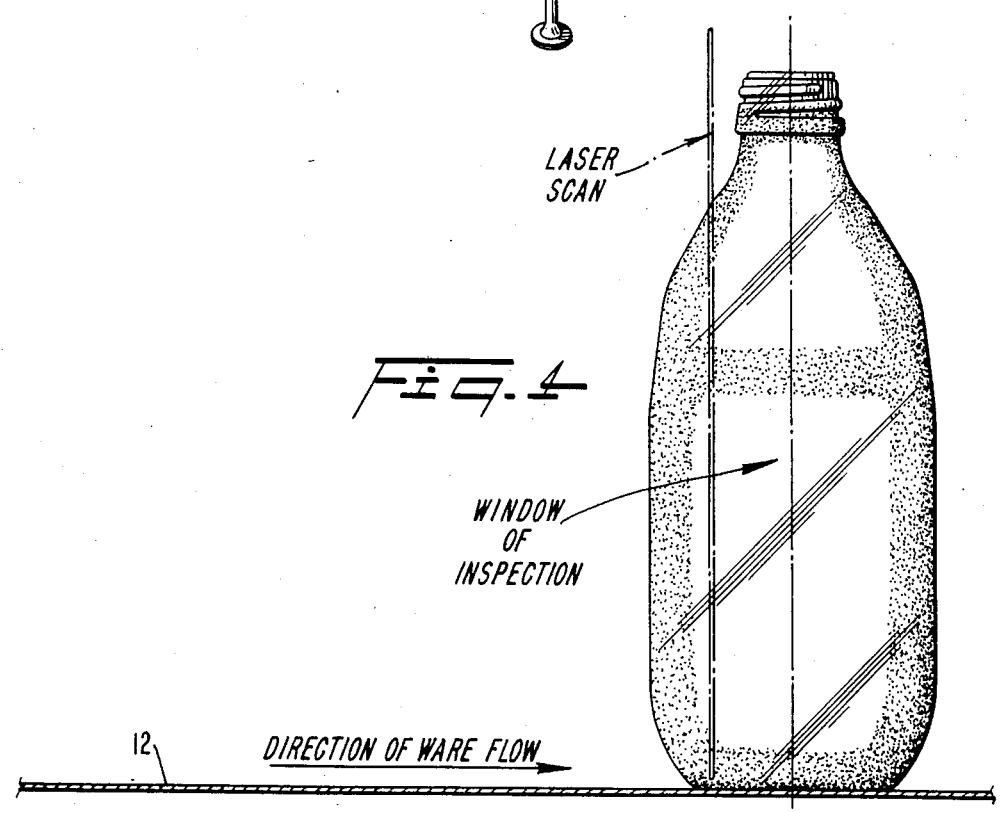
FIG. 4 is a side view of a bottle illustrating an inspection window.

Referring to FIG. 4, an example of a bottle that is to be inspected and the location of such a window thereon is shown. When the system is first initialized, a calibration model of known dimensions is conveyed through the inspection zones where it is scanned. The filtered photosensor 68 in the central cell detects the influence of the edge of the model on the laser beam and provides a signal to the synchronization and control circuit 80. This circuit passes the signal to the microprocessor, which processes it to determine the profile of the bottle. More particularly, each vertical excursion of the laser beam can be divided into a number of increments, e.g., 255 segments. For each excursion, the microprocessor determines during which increment of the excursion the detected light level of the incident beam changes by a predetermined amount, to ascertain the location of the edge of the bottle. After the bottle has been completely conveyed past the slot 16 so that it is scanned in its entirety, the microprocessor can determine a profile for the bottle and store it in memory.

During subsequent scans of bottles to inspected, the microprocessor selectively enables and disables each of the amplifier and count selection circuits 78 to define a dynamic window of inspection. This window is defined by vertical and horizontal parameters which can be selected by the operator. The vertical parameter can be expressed in terms of units of length, e.g., inches, and the horizontal parameter is preferably expressed in terms of degrees of the bottle circumference. Referring to the example of FIG. 4, the unshaded area in the central portion of the bottle represents the inspection window. Starting from the top of the bottle, this window might be defined as follows:

| Height (inches) | Width (degrees) |
|---|---|
| 0.0–0.75 | 0° |
| 0.75–2.5 | 60° |
| 2.5–3.0 | 0° |
| 3.0–6.0 | 90° |
| 6.0–bottom | 0° |

The microprocessor, in response to a scanner sync signal from the scanner driver circuit 46, which is indicative of the instantaneous angular orientation of the scanner mirror, disables the amplifier and count selection circuits during the portion of each scan in which the laser beam is in the shaded portion of the bottle and enables the circuits as the beam traverses the inspection window.

A separate window can be defined for each of the amplifier and count selection circuits so as to detect different types of faults in different areas of the bottle. Furthermore, as shown in FIG. 4, each vertical trace of the scanning beam can be divided into a number of adjustable horizontal inspection bands. Thus, for example, if it is known that the bottle is to be embossed in a certain area, the amplifier and count selection circuit or circuits which might detect this feature as a fault can be turned off as the beam scans that portion of the bottle. The inspection window for each of the selection circuits 78 can be displayed on a CRT monitor or a printer for the convenience of the operator.

Referrig to FIG. 5, each of the amplifier and count selection circuits 78 amplifies an incoming signal from one of the photodetectors in an amplifier 86 and compares its amplitude to a threshold value in a comparator 88. The gain of the amplifier can be user-adjusted by means of a potentiometer 90. Each time that the amplitude of the signal crosses the threshold during one vertical scan of the laser beam, a defect signal is generated and sent to a vertical occurrence comparator circuit 92. This circuit is selectively enabled and disabled by the microprocessor in accordance with the inspection window. The vertical occurrence comparator circuit, in response to a scan signal from the microprocessor or from the scanner phase control circuit 48, counts the number of flaw signals that are generated during each vertical trace of the laser beam. If the number of detected flaws during a scan is equal to or greater than a user-selected count, the comparator circuit 92 generates a signal which is presented to a horizontal occurrence counter 94. Within the horizontal occurrence counter, the number of scans for which the comparator circuit 92 generates a signal is counted and compared to a second user-selected count. If the number of counted scans equals or exceeds this second value, a signal is presented to a reject circuit 96. The reject circuit 96 issues a signal which is sent to a reject module 98 (FIG. 3) as well as counted in a reject counter 100. The reject counter 100 accumulates the number of bottles that are rejected by that selection circuit.

To provide the operator with an instantaneous indication of the status of the bottle analysis, the user-selected horizontal count value is converted to an analog signal in a digital-to-analog converter 102 and presented as a reference signal to a bar graph driver and display circuit 104. The actual count accumulated in the horizontal occurrence counter 94 is also converted into an analog signal, by means of a second digital-to-analog converter 106, and presented to a peak detector 108. The peak detector selects the peak value of the accumulated count for each bottle and provides it as a data signal to the driver and display circuit 104. This value is displayed on a bar display as a percentage of the reference count. Thus, when the accumulated count equals or exceeds the user-selected value, the bar graph will be fully illuminated to indicate that the bottle is being rejected.

The count which is determinative of a reject signal for each selection circuit 78 can be generated in one of three different modes of operation. Two of these modes determine the presence of a defect on the basis of the number of vertical scans in which a flaw signal is generated, in either a consecutive or nonconsecutive fashion. In the consecutive mode, a defect signal must be generated at least once per scan for each of a preselected number of consecutive scans. Thus, in this mode the vertical occurrence comparator circuit 92 provides a signal to the horizontal occurrence counter 94 only for each of two or more consecutive scans on which the user-selected count is equalled or exceeded. If the count is exceeded on one scan but not on the next, the comparator circuit 92 sends a reset signal to the counter 94. In the non-consecutive mode, it is only necessary that a flaw detection signal be generated during each of a predetermined number of scans across the window in order to cause a reject signal to be produced. Accordingly, in this mode each scan which results in the vertical count number being equalled or exceeded is indicated to the counter 94, regardless of whether the scans are consecutive. If the inspection window for a particular selection circuit 78 is divided into two vertically separated portions, it may be desirable to require that a flaw signal appear during the same portion of each of the scans, i.e. within the same section of a window, in order for a reject signal to be generated, thereby providing greater resolution.

In the third mode of operation, the total number of flaw signals that are generated is the determining factor, regardless of whether the flaw signals occurred during the same scan or on different scans. Thus, in this mode each flaw signal generated by the comparator 88 is presented to the horizontal occurrence counter 94 and counted therein.

As noted above and shown in FIG. 4, it is possible to divide the inspection window into two or more horizontal bands by disabling the associated count selection circuit 78 during a portion of each vertical trace of the laser beam. This may be necessary when the portion of the bottle contains certain features, e.g. a spiral design, which would be detected as a flaw. However, in some situations, it may be more desirable to inspect this portion of the bottle rather than blank out the inspection window in that area, yet account for design aspects of the bottle which might generate a flaw signal. This feature of the invention is accomplished by controlling the gain of the count selection circuit in accordance with the vertical position of the laser beam. To this end, the threshold value against which the incoming photosensor signal is compared can be adjusted under the control of the microprocessor. For example, the threshold might be established by means of a d.c. bias signal presented to one input terminal of the comparator 88. The amplitude of this d.c. bias signal can be adjusted by the microprocessor during each vertical trace of the laser beam to increase the threshold level, and thereby decrease the sensitivity of the circuit, as the beam scans the portion of the bottle having a design feature such as a curve or knurl which could accidentally cause a flaw signal to be generated.

Alternatively, this same result can be provided by adjusting the gain of the comparator 88 or the gain of the signal amplifier 86. Thus, under microprocessor control the criterion for flaw signal generation can be dynamically adjusted during the scanning of the beam for each individual circuit 78 to enable bottles having different design features to be fully inspected.

In addition, the microprocessor can adjust the sensitivity of all of the circuits 78 and 80 in accordance with any detected changes in the intensity of the laser beam. More particularly, during the initial portion of each scan, before the beam encounters the bottle, full intensity light will be detected in the center cell by the filtered photosensor 68. The amplitude of the detected light signal during this portion of the scan may decrease over time, for example due to the accumulation of dirt on the optical components and aging of the electrical components. This phenomenon can be detected in the control circuit 80 and used by the microprocessor to adjust the sensitivity of all of the defect detection circuits.

The reject module 98 controls the reject signal that is supplied to the solenoid for controlling one of the air valves 18 or 34. This module can be provided with delay and duration adjustments so that the time of generation and length of the reject signal is coordinated to the location and size of the defective bottle on the conveyor. The reject module 84 can also include a counter which accumulates the total number of containers rejected by the corresponding zone in the inspection station.

In the embodiment of the invention illustrated in FIG. 3, five photosensors are shown connected to seven amplifier and count selection circuits respectively labelled 2-8 as well as to the synchronization and control circuit 80. An example of the particular photodetector to which each of the circuits 78 and 80 can be connected, as well as the threshold and count settings for these circuits to detect particular types of defects, is illustrated in the following table:

TABLE 1
CONTAINER DEFECT SIGNAL PROCESSING

| Amplifier No. | Detection Chamber Cell | Container Defect | Defect Effect On Laser Beam | Amplifier Setting for Container Rejection | Remarks |
|---|---|---|---|---|---|
| 1 | Center Cell (Detector 68) | Dark container | Attenuation | — | This Amplifier is utilized for bottle edge detection to define the inspection window and for system synchronization. |
| 2 | Center Cell | Water marks Light marks | Refraction | High Gain High Count | |
| 3 | Top Cell | Birdswing Body marks (horizontal) Blisters Some white stones | Dispersion | High Gain Low Count | Amplifier must receive defect signal from top cell and defect signal from No. 8 amplifier (refraction pickup) to reject container. |
| 4 | Center Cell (Detector 64) | Birdswing end caps Black spots Stones Blisters Stuck glass Cracked container | Blocked beam - cell goes dark | Low Gain Low Count | |
| 5 | Center Cell (Detector 64) | Dirt Body marks Birdswing Cracked container | | High Gain High Count | |
| 6 | Center Cell (Detector 66) | Mottled container Cold mold Swab ware | Attenuation | High Gain High Count (non-consecutive) | Evaluates overall appearance of container. |
| 7 | Bottom Cell | Blowouts Birdswings Birdswing end caps Folds Body marks Slugs Washboards | Refraction | Low Gain Low Count | |
| 8 | Bottom Cell | Blowouts Body marks | | High Gain High Count | |

From the foregoing table, it will be appreciated that the present invention is capable of detecting a number of different types of flaws that are commonly encountered in transparent containers. Furthermore, the synchronization and control circuit 80 can be used to inspect the bottles for dimensional defects. As each bottle passes through the inspection zone, the edge detection signals generated by the control circuit 80 can be compared with those stored in memory. If a discrepancy exists due to improper bottle height, diameter or profile, e.g. a leaning bottle, a reject signal can be generated. The circuit 80 can also be used to count the total number of bottles that are processed.

In addition to rejecting defective bottles, the present invention provides the capability of supplying feedback information which can be used to isolate the source of a defect and thereby correct it to increase productivity. For example, if an inspection window is divided into a number of horizontal bands, the reject count which is accumulated in each of the circuits 78 might be broken down in accordance with the particular band in which the flaws were detected. Thus, if the same type of flaw consistently occurs in the same area of each rejected bottle, statistical information regarding the containers rejected by each module can be used to spot a trend and used to ascertain the possible source of the flaw and correct it.

It will be appreciated by those of ordinary skill in the art that the present invention can be embodied in other specific forms without departing from the spirit or essential characteristics thereof. The presently disclosed embodiment is therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Apparatus for detecting defects in transparent articles, comprising:
   means for scanning a beam of light in a first direction a plurality of times so that the scanned beam of light traverses an article during each scan;
   means for linearly moving the article and the scanned beam of light relative to one another in a second direction so that the beam traverses different portions of the article on successive scans;
   optical means for focussing light passing through the article onto a diffusing screen, said screen being located at the focal length of said optical means;

a plurality of photodetectors disposed adjacent said screen for respectively detecting the intensity of light at different portions of said screen;

threshold detection and counting means connected to said photodetectors for determining the number of times the intensity of light detected by each of said photodetectors crosses respective thresholds;

means for synchronizing said threshold detection and counting means with said scanning means so that said determination takes place only during a predetermined portion of each scan as said light beam traverses the article; and means responsive to said threshold detection and counting means for generating a reject signal when said number of times is at least equal to a predetermined criterion value.

2. The apparatus of claim 1 further including a chamber disposed adjacent to said screen, said chamber being divided into a plurality of cells with at least one of said photodetectors being located in each cell.

3. The apparatus of claim 1 wherein said threshold detection and counting means includes first means for counting the number of times a threshold is crossed during each scan of the beam and second means for counting the number of scans during which the threshold is crossed.

4. The apparatus of claim 3 wherein said second means counts the number of consecutive scans during which the threshold is crossed.

5. The apparatus of claim 3 wherein said synchronizing means enables one of said first and second counting means to count crossings of a threshold only during said predetermined portion of each scan of the beam of light.

6. The apparatus of claim 1 wherein said optical means includes a lens for focussing all light which passes through a article unimpeded by a defect onto a predetermined area on said screen.

7. The apparatus of claim 6 wherein at least one of said threshold detection and counting means and an associated photodetector is responsive to a decrease in the intensity of light projected onto said predetermined area on said screen to generate a flaw signal, and another of said threshold detection and counting means is responsive to the projection of light onto a portion of the screen outside of said area to generate a flaw signal.

8. The apparatus of claim 1 further including means for dynamically varying at least one of said thresholds during each scan of said beam in accordance with the position of the beam during the scan.

9. The apparatus of claim 1 further including means for adjusting said thresholds in response to changes in the detected intensity of the laser beam during a portion of its scan in which it does not pass through an article.

10. The apparatus of claim 1 wherein said scanning means causes the beam of light to sinusoidally traverse the article.

11. A method for detecting the presence of a fault in a transparent container, comprising the steps of:
scanning a beam of light across the container;
employing an optical means for focussing light passing through the container onto a diffusing screen, said screen being located at the focal length of said optical means;
detecting the intensity of light falling on different predetermined portions of the screen;
comparing the detected intensity at each of said portions with a predetermined threshold for that portion;

counting the number of times that the detected light intensity crosses the threshold during scanning of the beam; and generating a signal to indicate the presence of a fault when said number of times is at least equal to a predetermined value.

12. The method of claim 11 further including the step of synchronizing said comparing step with the scanning of the beam so that said comparing takes place only while said beam is traversing a predetermined area on the container.

13. The method of claim 11 wherein said light is focussed onto the screen in a manner such that all light which passes through the container unaffected by a flaw is projected onto one portion of the screen and light which is refracted or dispersed by a flaw is projected onto another portion of the screen.

14. The method of claim 12 wherein said predetermined area on the container is divided into at least two sections, and further including the steps of determining which section of each faulty container contains the fault that results in the generation of said signal, counting the total number of generated signals, and classifying the counted signals in accordance with respective sections of the containers.

15. The method of claim 11 further including the steps of determining the position of the beam each time a preselected intensity level is crossed during the scanning of a model container, storing the determined positions to obtain a dimensional profile for the container, and comparing the position of the beam when its intensity crosses said preselected level with said stored position during subsequent scanning of other containers to thereby detect dimensional defects in said other containers.

16. The method of claim 11 wherein the beam of light traverses the container a plurality of times during scanning, and wherein said counting step includes counting the number of times the detected light intensity crosses the threshold during each traversal of the container and the number of traversals in which the counted number of times exceeds a preselected number, and further wherein said fault signal is generated when the counted number of traversals is at least equal to said predetermined value.

17. The method of claim 16 wherein said counting step comprises counting only consecutive traversals in which the counted number of times exceeds said preselected number.

18. The method of claim 11 further including the step of dynamically adjusting said threshold in accordance with the position of the beam during scanning.

19. The method of claim 11 wherein said comparing and counting steps are carried out for each of a number of different thresholds, and said fault signal is generated when the count for any one of said thresholds equals a predetermined value associated with that threshold, to thereby detect a number of different types of flaws.

20. A system for inspecting a container to detect the presence of a flaw, comprising:
means for continuously moving a container along a path of travel;
a first inspection zone including means for scanning a portion of the container with a beam of light, means for collecting light passing through the container and focussing it upon a screen, means for detecting the location and intensity of light focussed on the screen, and means for processing the detected light to selectively generate a first reject signal;

container rotating means located downstream of said first inspection zone for rotating said container 90° about its longitudinal axis; and a second inspection zone located downstream of said rotating means and including means for scanning a portion of the container with a beam of light, means for collecting light passing through the container and focussing it upon a screen, means for detecting the location and intensity of light focussed on the screen, and means for processing the detected light to selectively generate a second reject signal.

21. The system of claim 20 wherein said container moving means comprises a conveyor and said container rotating means includes a pair of belts respectively disposed on opposite sides and parallel to said conveyor for engaging a container as it passes between them on said conveyor, and means for moving one of said belts faster than said conveyor and moving the other of said belts slower than said conveyor so as to rotate the container as it moves at the speed of said conveyor.

22. Apparatus for detecting defects in transparent articles, comprising:

means for scanning a beam of light a plurality of times so that the beam traverses different portions of an article on successive scans;

optical means for focussing light passing through the article onto a diffusing screen, said screen being located at the focal length of said optical means;

a plurality of photodetectors disposed adjacent said screen for respectively detecting the intensity of light at different predetermined areas of said screen;

threshold detection means connected to said photodetectors for determining when the intensity of light detected by each of said photodetectors crosses respective thresholds;

means for synchronizing said threshold detection with said scanning means so that said determination takes place only during a predetermined portion of each scan as said light beam traverses the article; and means responsive to said threshold detection for generating a reject signal.

23. The apparatus of claim 22 further including means for dynamically varying at least one of said thresholds during each scan of said beam in accordance with the portion of the article being scanned.

24. Apparatus for detecting defects in transparent articles, comprising:

means for scanning a beam of light a plurality of times so that the beam traverses different portions of the article on successive scans;

optical means for focussing light which passes through the article substantially unimpeded by a defect onto a predetermined area on a diffusing screen, said screen being located at the focal length of said optical means;

a plurality of photodetectors disposed adjacent said screen for respectively detecting the intensity of light at said predetermined area of said screen and at another area outside of said predetermined area;

threshold detection means and counting means connected to said photodetectors for determining the number of times the intensity of light detected by each of said photodetectors crosses respective thresholds; and means responsive to said threshold detection and counting means for generating a reject signal when said number of times is equal to or greater than a predetermined criterion value.

25. The apparatus of claim 24 further including means for dynamically varying at least one of said thresholds during each scan of said beam in accordance with the portion of the article being scanned.

26. Apparatus for detecting defects in transparent articles, comprising:

means for scanning a beam of light so that the scanned beam of light traverses an article;

optical means for focussing all light which passes through an article unimpeded by a defect onto a predetermined area on a diffusing screen;

a plurality of photodetectors disposed adjacent said screen for respectively detecting the intensity of light at different portions of said screen;

first threshold detection and counting means connected to one of said photodetectors for generating a flaw signal when the intensity of light focussed onto said predetermined area falls below a threshold value and for counting said flaw signals;

second threshold detection and counting means connected to another of said photodetectors for generating a flaw signal when light is at a portion of the screen outside of said area and for counting said flaw signals;

means for synchronizing said threshold detection and counting means with said scanning means so that said counting takes place only as said light beam traverses a predetermined portion of the article; and means responsive to said threshold detection and counting means for generating a reject signal when said number of times is at least equal to a predetermined criterion value.

* * * * *